(12) United States Patent
Fritsch et al.

(10) Patent No.: US 10,502,291 B2
(45) Date of Patent: Dec. 10, 2019

(54) ELECTRICALLY DRIVEN DEVICE

(71) Applicant: Braun GmbH, Kronberg (DE)

(72) Inventors: Thomas (NMN) Fritsch, Eppstein (DE); Andreas (NMN) Kramp, Bad Camberg (DE); Norbert (NMN) Schaefer, Frankfurt am Main (DE)

(73) Assignee: BRAUN GMBH, Kronberg (DE)

( * ) Notice: Subject to any disclaimer, the term of this patent is extended or adjusted under 35 U.S.C. 154(b) by 0 days.

(21) Appl. No.: 15/715,109

(22) Filed: Sep. 25, 2017

(65) Prior Publication Data
US 2018/0087632 A1   Mar. 29, 2018

(30) Foreign Application Priority Data

Sep. 28, 2016  (EP) ..................................... 16191024

(51) Int. Cl.
*F16H 21/40* (2006.01)
*A61C 17/34* (2006.01)
(Continued)

(52) U.S. Cl.
CPC ............. *F16H 21/40* (2013.01); *A61C 1/185* (2013.01); *A61C 17/221* (2013.01); *A61C 17/34* (2013.01); *A61C 17/3481* (2013.01); *H02K 7/075* (2013.01)

(58) Field of Classification Search
CPC ......... F16H 21/40; F16H 21/50; A61C 1/185; A61C 17/211; A61C 17/34;
(Continued)

(56) References Cited

U.S. PATENT DOCUMENTS 3,233,265 A    8/1966  Hartmann
3,474,795 A   10/1969  Hantman
(Continued)

FOREIGN PATENT DOCUMENTS

DE        3544256       6/1987
JP     2001198145       7/2001
(Continued)

OTHER PUBLICATIONS

European Search Report, dated Mar. 7, 2017; 9 pages.

*Primary Examiner* — Bobby Rushing, Jr.
(74) *Attorney, Agent, or Firm* — Vladimir Vitenberg

(57) ABSTRACT

An electrically driven device includes a housing, an electric motor with a drive shaft having a first rotary axis and a drive pin connected to the drive shaft eccentrically with respect to the rotary axis, and a driven shaft having a second rotary axis and mounted in the housing for performing a pivoting about the second rotary axis. The driven shaft is coupled to the drive shaft by a gear mechanism including a scotch yoke mechanism converting a rotary motion of the drive shaft into a reciprocating motion of the driven shaft. The scotch yoke mechanism includes a cross slider having a sliding support extending perpendicular to the first rotary axis and receiving the drive pin either directly or through a sliding block with a bearing receiving the drive pin. The cross slider is guided in the housing by at least two pivotable links. The driven shaft is coupled to the cross slider by an arm, converting a rotary motion of the drive shaft into a reciprocating of the driven shaft.

12 Claims, 4 Drawing Sheets

(51) Int. Cl.
  *H02K 7/075* (2006.01)
  *A61C 1/18* (2006.01)
  *A61C 17/22* (2006.01)

(58) Field of Classification Search
  CPC ............ A61C 17/3418; A61C 17/3436; A61C 17/3481; H02K 7/075
  USPC ........ 74/25, 27, 38, 45, 48, 49, 50; 15/22.4; 30/43.7, 43.8, 215, 218; 433/118, 122
  See application file for complete search history.

(56) References Cited

U.S. PATENT DOCUMENTS

| | | | |
|---|---|---|---|
| 3,562,566 A * | 2/1971 | Kircher | A61C 17/3472 15/22.1 |
| 3,699,952 A * | 10/1972 | Waters | A46B 13/02 15/22.1 |
| 4,506,400 A | 3/1985 | Klein | |
| 4,628,605 A * | 12/1986 | Clowers | B23D 49/165 30/393 |
| 5,283,921 A * | 2/1994 | Ng | A61C 17/22 15/145 |
| 5,311,633 A | 5/1994 | Herzog et al. | |
| 5,381,576 A | 1/1995 | Hwang | |
| 5,689,850 A | 11/1997 | Shekalim | |
| 5,822,821 A | 10/1998 | Sham | |
| 5,974,615 A | 11/1999 | Hilfinger et al. | |
| 6,237,178 B1 | 5/2001 | Krammer | |
| 7,120,960 B2 * | 10/2006 | Hilscher | A61C 17/3472 15/22.1 |
| 7,614,107 B2 | 11/2009 | Cobabe | |
| 7,636,976 B2 | 12/2009 | Banning | |
| 7,810,200 B2 * | 10/2010 | Fujimoto | A61C 17/3445 15/22.2 |
| 7,861,348 B2 | 1/2011 | Chan | |
| 8,256,055 B2 * | 9/2012 | Kressner | A61C 17/22 15/22.1 |
| 8,443,476 B2 | 5/2013 | Hilscher | |
| 8,875,335 B2 | 11/2014 | Kloster et al. | |
| 8,943,634 B2 | 2/2015 | Sokol | |
| 2003/0131427 A1 | 7/2003 | Hilscher | |
| 2006/0101598 A1 | 5/2006 | Fujimoto et al. | |
| 2012/0284937 A1 | 11/2012 | Kloster | |
| 2018/0087631 A1 | 3/2018 | Kramp | |
| 2018/0087633 A1 | 3/2018 | Fritsch | |
| 2018/0091018 A1 | 3/2018 | Fritsch | |
| 2018/0091019 A1 * | 3/2018 | Fritsch | A61C 1/185 |

FOREIGN PATENT DOCUMENTS

| | | |
|---|---|---|
| JP | 2013226202 | 11/2013 |
| KR | 20080069373 | 7/2008 |
| WO | WO2011077285 | 6/2011 |

* cited by examiner

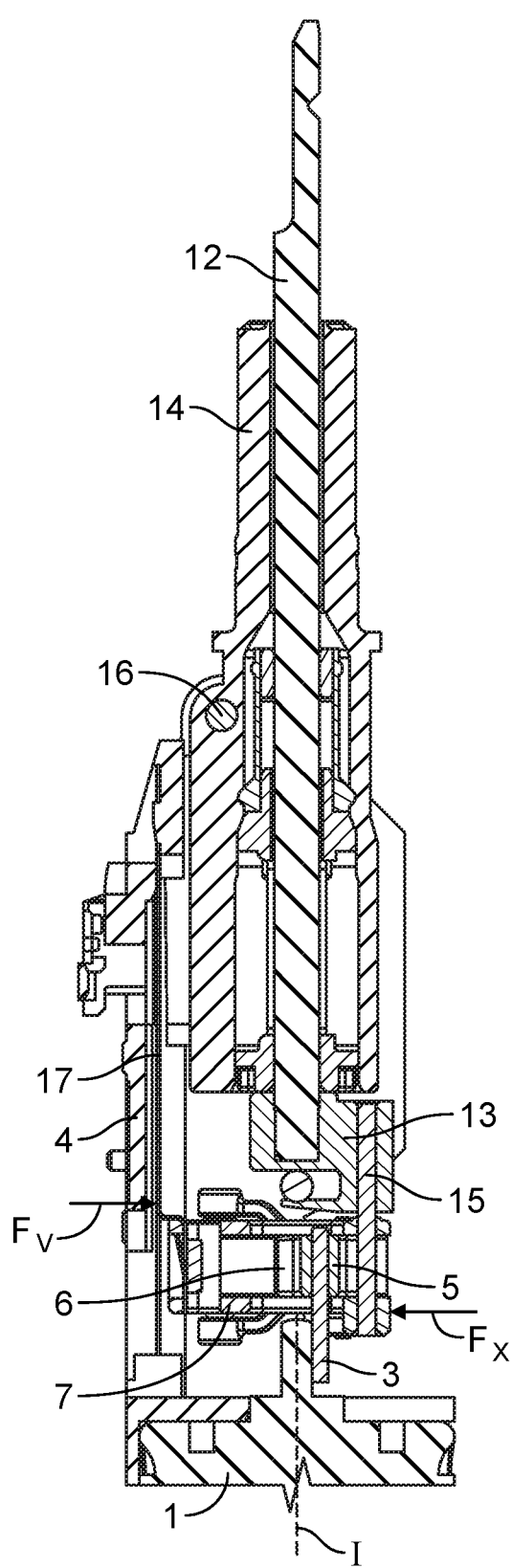
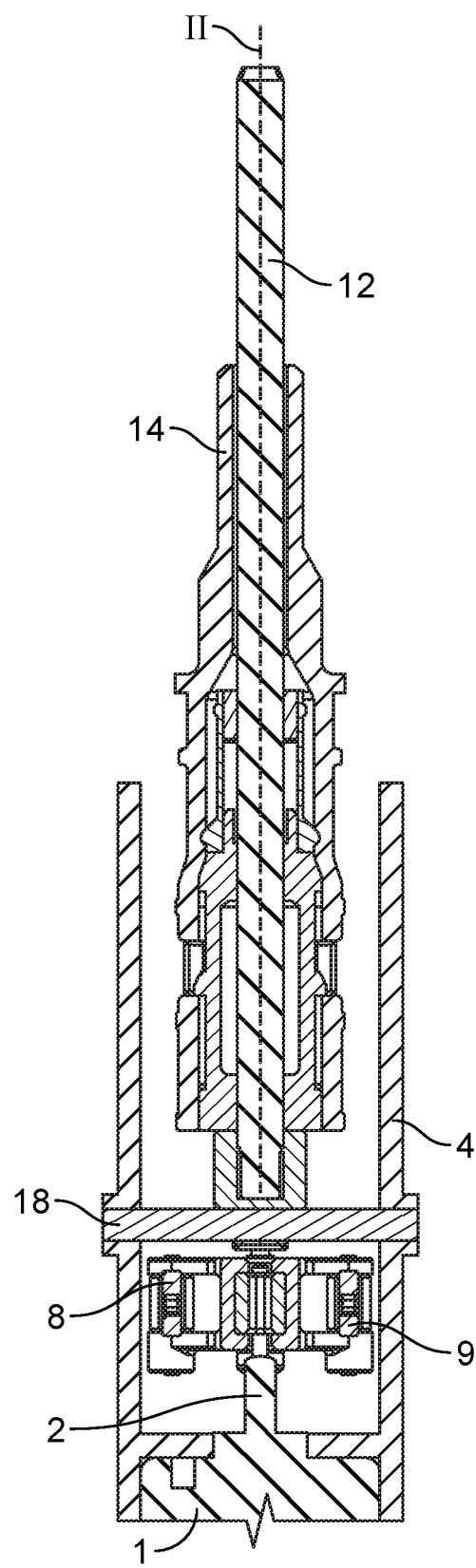
FIG. 1
FIG. 2

ELECTRICALLY DRIVEN DEVICE

FIELD OF THE INVENTION

The present invention is concerned with an electrically driven device, for example an electric toothbrush, an electric hair removal device or an electric skin treatment device.

BACKGROUND OF THE INVENTION

An electric toothbrush with a drive mechanism comprising gearwheels is known for example from DE 39 37 854 A1. The drive mechanism converts a continuous rotary movement of the drive shaft of an electric motor into a reciprocating pivoting of a driven shaft. EP 0 850 027 B1 and EP 1 357 854 B1 disclose further drive mechanisms with gearwheels wherein the mechanisms further generate an additional pivoting of the drive shaft about a swiveling axis. The use of gearwheels may contribute to increased sound emissions.

US 2006/0101598 A1 discloses an electric toothbrush with a scotch yoke mechanism converting a continuous rotary movement of the drive shaft of an electric motor into a reciprocating longitudinal displacement of a driven shaft.

Further, U.S. Pat. No. 5,381,576 describes an electric toothbrush comprising a housing, an electric motor with a drive shaft having a first rotary axis and a drive pin connected to the drive shaft eccentrically with respect to the rotary axis, and a driven shaft having a second rotary axis and mounted in the housing for performing a pivoting about the second rotary axis. The driven shaft is indirectly coupled to the drive pin by a gear mechanism converting a rotary motion of the drive shaft into a reciprocating pivoting of the driven shaft. The gear mechanism comprises an elastically deformable transmission member.

It is an object of the present disclosure to provide an electrically driven device with reduced sound emissions.

SUMMARY OF THE INVENTION

In accordance with one aspect there is provided an electrically driven device comprising a housing, an electric motor mounted in the housing and comprising a drive shaft having a first rotary axis, a driven shaft having a second axis and mounted in the housing for performing a movement relative to the housing. The driven shaft may be indirectly coupled to the drive shaft by means of a gear mechanism comprising a scotch yoke mechanism, i.e. a slotted link mechanism, converting a rotary motion of the drive shaft into a reciprocating pivoting motion of the driven shaft. A drive pin may be connected to the drive shaft eccentrically with respect to the rotary axis. The scotch yoke mechanism comprises a cross slider having a sliding support which extends perpendicular to the first rotary axis and which receives the drive pin either directly or by means of a sliding block having a bearing receiving the drive pin. The cross slider is guided in the housing by means of at least two pivotable links which may be directly coupled to the housing or indirectly, e.g. via an adapter and/or a spring. The driven shaft is coupled to the cross slider by means of a pivotable arm. The eccentric drive pin may be directly connected to the drive shaft or may be indirectly connected to the drive shaft, e.g. by means of one or more interposed elements and/or a gear.

In accordance with a further aspect, an electrically driven device with a housing and a drive shaft having a first rotary axis comprises a driven shaft pivotably mounted in the housing by means of a rocker frame. The rocker frame may be pivotable with respect to the housing about a pivoting axis which is perpendicular to the first rotary axis. An elastically deformable element may be provided between the housing and the rocker frame biasing the rocker frame into a rest position.

BRIEF DESCRIPTION OF THE DRAWINGS

FIG. 1 shows a sectional view of a device according to a first embodiment;

FIG. 2 shows a sectional view of the device of FIG. 1 perpendicular to the view of FIG. 1;

DETAILED DESCRIPTION OF THE INVENTION

Figure 3A:
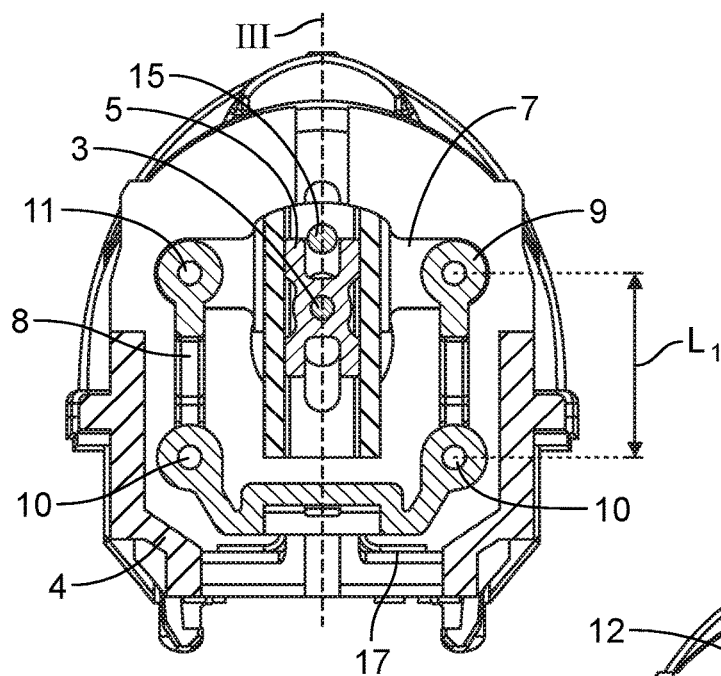
FIG. 3a-c show further sectional views of the device of FIG. 1 perpendicular to the views of FIGS. 1 and 2.
Figure 3B:
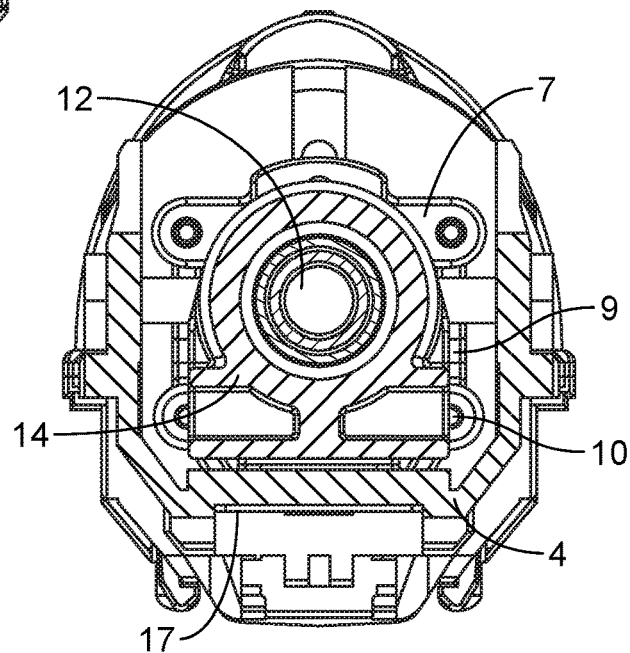
Figure 3C:
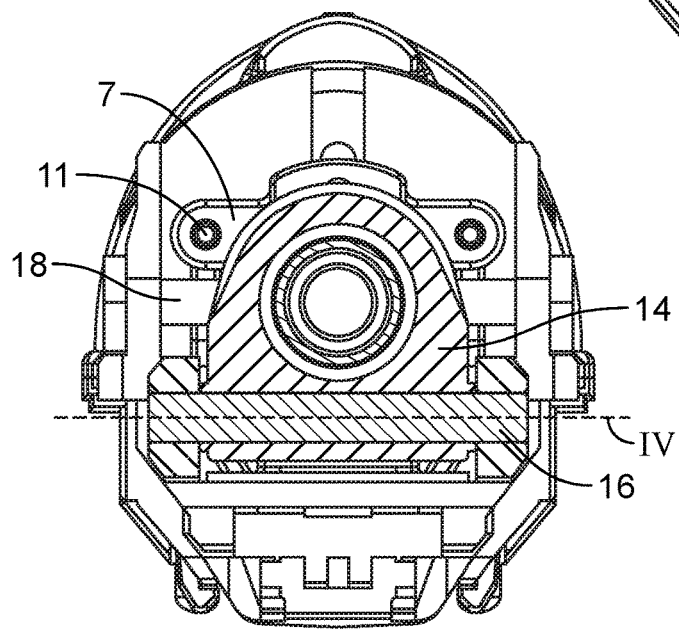

Current toothbrush drive systems performing an oscillating pivoting of the cleaning element, e.g. a bristle, are perceived as being too loud. In particular, it is desirable to provide an electrically driven device with sound emissions below 55 dB(A) sound power level, especially at current drive frequency of 83 Hz. An important factor for noise is the form of the motion over time. The velocity is the first derivative of the displacement, the acceleration the second derivative of the motion. Higher accelerations and therefore inertia forces occur if the wave form is not a sine wave or harmonic. These periodic forces translate into bearing reaction forces and thus create an excitation to the structure of the device and this can cause undesired noise of elements oscillating in their natural frequency. Another source of noise is two bodies hitting each other and creating a rattling noise. This occurs for example in cam driven systems.

In accordance with one aspect, a gear mechanism is provided converting a rotary motion of the drive shaft into a reciprocating pivoting of the driven shaft, preferably a sinusoidal movement of the driven shaft or a substantially sinusoidal movement of the driven shaft. This contributes in reducing the noise generated in use of the device.

According to an aspect, the gear mechanism comprises a scotch yoke mechanism with the cross slider being guided in the housing by means of at least two pivotable links. The scotch yoke mechanism of the gear mechanism may convert a continuous rotary motion of the drive shaft into a sinusoidal reciprocating movement of the cross slider. The movement of the cross slider may be a rotational motion which may be close to a linear motion guided by a parallel lever design in the form of a parallelogram by means of the at least two pivotable links. For example, each of the at least two pivotable links is pivotably hinged to a bearing point of the housing and pivotably hinged to a bearing point of the cross slider such that the cross slider is guided to be moveable on a curved track with respect to the housing. The distance between the bearing point of the housing and the bearing point of the cross slider may be identical for each of the pivotable links. The cross slider may have a cylindrical opening defining the sliding support of the sliding block with a long hole provided in the sliding support receiving the drive pin.

The driven shaft is coupled to the cross slider by means of a pivotable arm. The pivotable arm translates the rotational motion of the cross slider into an oscillating pivoting about the second rotary axis of the driven shaft. For example, the pivotable arm may be pivotably hinged to a bearing point of the cross slider and rotationally constrained to an anchorage point of the driven shaft.

The electrically driven device may further comprise a sliding block having a bearing receiving the drive pin. For example, the sliding block may be axially guided in the sliding support of the cross slider. In other words, the gear mechanism may work similar to the scotch yoke mechanism translating a continuous rotation of the drive pin into a reciprocating pivoting movement of the cross slider and of the driven shaft. As an alternative to the provision of a sliding block within the cross slider, the drive pin may directly engage the sliding support of the cross slider, e.g. having the form of a slotted hole.

The housing may be a single, unitary component part suitable for encasing and/or mounting further component parts of the device. In other embodiments, the housing may comprise different component parts, for example an outer shell, an insert, a chassis and/or a frame.

The electrically driven device may be a platform for different applications, for example as a toothbrush, as a skin treatment device or as a hair removal device. In some embodiments it may be desirable that the driven shaft only performs an oscillating pivoting about the second rotary axis without any superimposed further movements. This may be achieved by choosing the distance of the pivotable links between the bearing point of the housing and the bearing point of the cross slider to be identical to the distance of the pivotable arm between the bearing point of the cross slider and the second rotary axis of the driven shaft. For example, the second rotary axis may be positioned on a straight line between the bearing point of the housing and the bearing points on the cross slider for the links and the arm may be positioned on a straight line, too. As an alternative, the arm may be arranged shifted with respect to the links.

In some other embodiments it may be desirable that the driven shaft not only performs an oscillating pivoting about the second rotary axis but rather performs a 3D motion, e.g. with a superimposed pivoting of the driven shaft. This may be achieved by choosing the distance of the pivotable links between the bearing point of the housing and the bearing point of the cross slider to be different from the distance of the pivotable arm between the bearing point of the cross slider and the second axis of the driven shaft. Due to these different lengths of the levers, an axial force $F_X$ is exerted on the driven shaft which may result in an additional motion of the driven shaft. In this respect, the driven shaft may be pivotably mounted in the housing, e.g. by means of a rocker frame which is pivotable with respect to the housing about a pivoting axis which is perpendicular to the first rotary axis and perpendicular to the extension of the sliding support.

For example, an elastically deformable element, e.g. a spring, may be provided between the housing and the rocker frame biasing the rocker frame into a rest position or a zero position with a biasing force $F_Y$. The spring may be a leaf spring or a cylindrical spring. The rest position may be defined by the elastically deformable element being in an unstressed condition, i.e. the biasing force $F_Y$ is zero. In addition or as an alternative, the rocker frame may be abutting a first stop in the rest position or zero position.

A switch or sensor may be provided and arranged in the housing such that the switch or sensor detects movement of the rocker frame with respect to the housing. In more detail, the switch or sensor may be arranged in the housing such that the switch or sensor detects movement of the rocker frame with respect to the housing exceeding a threshold movement. For example, a deviation from the rest position or zero position may be detected. If a force is applied on the driven shaft, for example via a brush head of a toothbrush, the rocker frame is pivoting about the axis and is displaced against the housing and/or a PCB mounted in the housing. This movement may be used to measure and control the applied pressure. The execution may be a threshold, where a switch is activated or a magnet and a hall sensor may be used to measure the displacement. Other options include optical means or inductive proximity sensors. The travel of the arm for the pressure sensor may be in the range of <0.5 mm to 2 mm, e g at a force of 0.5 to 4N.

The movement of the cross slider may generate an intermittent force $F_X$ in a direction perpendicular to the second axis which intermittent force $F_X$ is transmitted to the rocker frame via the pivotable arm and the driven shaft. The intermittent force $F_X$ may bias the rocker frame away from the rest position. To permit a 3D movement of the driven shaft, the intermittent force $F_X$ generated by the motion of the cross slider may exceed the biasing force $F_Y$ of the elastically deformable element.

According to one aspect, the rocker frame pivots relative to the housing with a constant amplitude and a varying force depending on the magnitude of a user force exerted on the driven shaft, for example a contact pressure of a toothbrush to the user's teeth. For example, if the rocker frame is in its rest position with respect to the housing with the elastically deformable element being unstressed, a user force exerted on the driven shaft may be directed opposite to the intermittent force $F_X$ generated by the motion of the cross slider and/or opposite to the biasing force $F_Y$.

A bar may be provided constrained to the housing and located at the end of the driven shaft facing towards the motor. This bar may prevent damages to the gear mechanism in case that the device is dropped falling onto the driven shaft.

The electrically driven device may comprise a standard DC motor. The motor may have a torque of at least 2 mNm, for example 2.5 mNm, at a speed of 4,800 to 7,200 rpm at a voltage of 3 to 4V. This voltage may be supplied by a Li-Ion battery or any other battery combination providing voltages above 3V and low internal resistance. In addition or as an alternative, the motor may be connected to the mains supply.

In the embodiment depicted in FIG. 1 a portion of an electrically driven device in the form of an electric toothbrush is shown. The device comprises an electric motor 1 with a drive shaft 2 rotating during use. A drive pin 3 is eccentrically attached to the drive shaft 2. Hence, the drive pin can be termed herein as "eccentric pin" (or simply "pin"). The motor 1 is constrained in a device housing 4 or a chassis mounted in the housing which is only partly visible in FIGS. 1 and 2. The drive shaft 2 defines a first rotary axis I. The pin 3 is coupled to a sliding block 5 such that the sliding block 5 follows movement of the pin 3. However, the pin 3 may be rotated within an aperture of the sliding block 5. The pin 3 in turn is guided in a sliding support 6 of a cross slider 7. The cross slider 7 is mounted in the housing 4 by means of two pivotable links 8 and 9. Each of the links 8 and 9 is pivotably hinged to a bearing point 10 of an adapter 4a, which may be coupled directly or indirectly to the housing 4, and pivotably hinged to a bearing point 11 of the cross slider 7. As can be seen in FIG. 3A, the links 8 and 9 each have the same length L1 between the respective bearing points 10 and 11.

Figure 5:
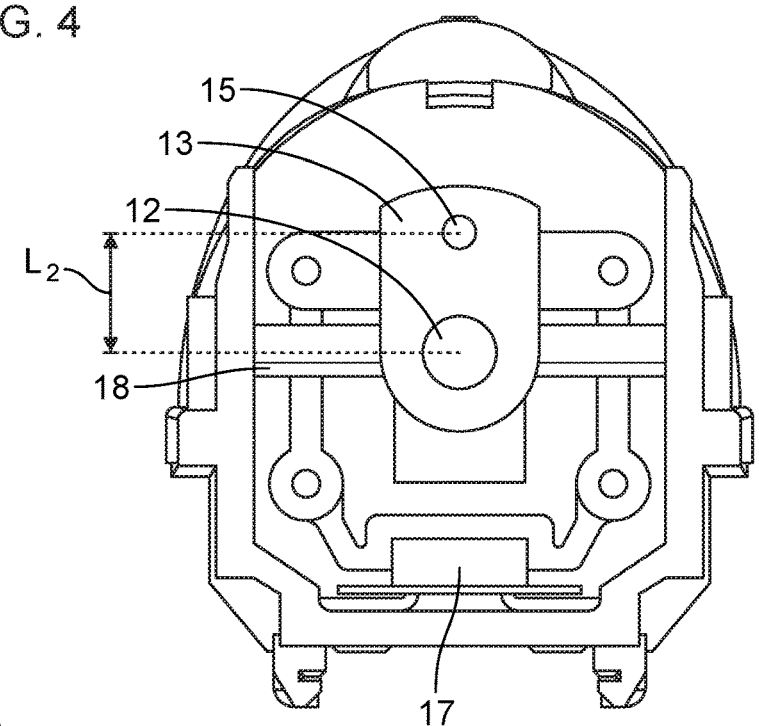
FIG. 5 shows a detail of the scotch yoke mechanism of the device of FIG. 1.

A driven shaft 12 is coupled to the cross slider 7 by means of an arm 13. The driven shaft 12 defines a second rotary axis II. The driven shaft 12 is rotatably guided in bearings of a rocker frame 14. The arm 13 is rotationally constrained to an anchorage point of the driven shaft 12. Further, the arm 13 is hinged to a bearing point of the cross slider 7, which bearing point is a pin 15 in the example depicted in the Figures. The arm 13 has a length $L_2$ between the second rotary axis II and the pin 15. As can be seen in FIG. 5, the length $L_1$ differs from the length $L_2$.

Figure 4:
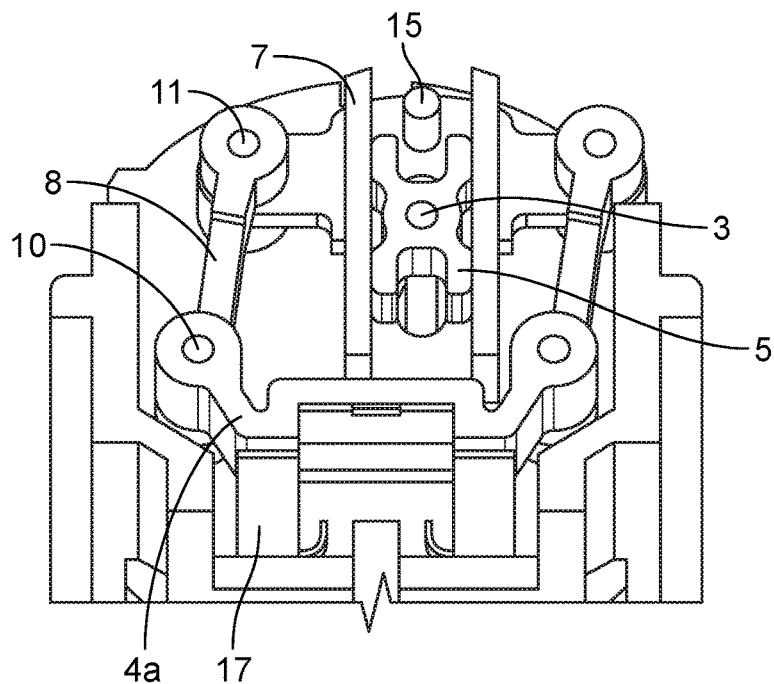
FIG. 4 shows a detail of the scotch yoke mechanism of the device of FIG. 1.

The rocker frame 14 is pivotably mounted in the housing 4 by means of a bar 16. Pivoting of the rocker frame 14 about bar 16 with respect to the adapter 4a is reacted by a leaf spring 17 which is arranged interposed between of the housing 4 and the rocker frame 14. Spring 17 may have a lateral support to the chassis of housing 4, for example spring loaded. This support avoids side to side movement of the rocker frame 14. As an alternative, a different type of an elastically deformable element 17 may be used, for example a cylindrical coil spring. Adapter 4a may be coupled to the housing 4 by means of spring 17 as shown in FIG. 4. The rocker frame 14 may be provided with an indicator which may be provided with a magnet. The position of the magnet, i.e. the displacement of the rocker frame, may be detected by means of a hall sensor (not shown). As an alternative, the indicator may activate a switch, an optical detector or an inductive proximity sensor.

A further bar 18 is constrained in the housing 4 at a position abutting or in close contact with the driven shaft 12 at the end of the driven shaft 12 facing towards the motor 1. This bar 18 is assembled directly under the driven shaft 12 to take up the forces created in a drop of the device on the driven shaft. To avoid axial movements a spring element may be molded into the connector arm 13 of the driven shaft. In other words, the arm 13 may have a C-form configuration in the sectional view of FIG. 1 engaging bar 18, with the lower section of the C-form being flexible. Another spring element is also possible.

As can be seen in FIG. 1, which shows the device in a rest position or a zero position, the first rotary axis I extends in parallel to the second rotary axis II. A third axis III is defined by the sliding support 6 within the cross slider 7. The third axis III is perpendicular to the first rotary axis I. A fourth axis IV is defined by bar 16. The fourth axis IV is perpendicular to the first rotary axis I and perpendicular to the third axis III.

In the following, operation of the device is explained in more detail with reference to the Figures. FIGS. 3a and 4 depict different positions of the sliding block 5 and the cross slider 7 during operation of the motor 1. The eccentric pin 3 welded to the motor shaft 2 is rotating. The pin 3 is mounted in a hole in the sliding block 5. The sliding block 5 is sliding in one direction in cross slider 7 and, thus, out of the rotational motion a side to side motion is created. This principle is similar to the scotch yoke mechanism or slotted link mechanism. The difference here is that the output is not a linear motion, but a rotational motion close to a linear motion guided by the parallel lever design with links 8 and 9 forming a parallelogram with a housing part and cross slider 7. In other words, the cross slider 7 is not guided in a longitudinal guidance, but oscillating around two pivot points 10. This is executed by a linkage with the two parallel link connectors 8 and 9 forming a parallelogram allowing an oscillating motion. Therefore a slight deviation from the sine wave form exists with an additional component/axis of motion.

FIG. 3a shows a first position of the drive shaft 2 and its eccentric pin 3. In this first position, sliding block 5 is located near pin 15 within sliding support 6. Further, cross slider 7 is in a center position with the third axis III of the sliding support 6 crossing the first rotary axis I. In FIG. 4 motor 1 rotated drive shaft 2 by 90°. By this rotation of pin 3 about the first rotary axis I, sliding block 5 is displaced within sliding support 6 away from pin 15. In addition, cross slider 7 is displaced to the right as seen in FIG. 4. Summarizing, rotation of motor 1 causes an oscillating sinusoidal motion of cross slider 7. Due to the links 8 and 9 cross slider 7 is guided on a curved, i.e. circular, path with respect to the housing 4. In a second step, this oscillating motion of cross slider 7 causes an oscillating pivoting of driven shaft 12 about the second rotary axis II by means of arm 13. The oscillating motion created in the cross slider 7 is transmitted to the driven shaft 12. For this purpose, the, e.g. metal, pin 15 is used, which is moving on a curve with the radius of the distance of the coupling arm 13.

Given that links 8 and 9 and in addition arm 13 are hinged to cross slider 7 with length $L_1$ differing from the length $L_2$ in the example shown in the Figures, displacement of the cross slider 7 results in a force $F_X$ acting on the driven shaft 12 and the rocker frame 14 which is pivotably mounted into a chassis of housing 4. For example, the biasing force $F_Y$ of the spring is smaller than the force $F_X$ generated during rotation of motor 1. In other words, the rocker frame 14 is driven pivoting about bar 16 against biasing force $F_Y$ of leaf spring 17 if no external force is exerted on the driven shaft 12 resulting in a 3D motion of the driven shaft 12. That is, the rocker frame 14 is held in its zero position shown in FIGS. 1 and 2. However, if a user exerts a force on the driven shaft 12, for example a contact pressure during use of a toothbrush, the force $F_X$ and the biasing force $F_Y$ act against the user exerted force.

In the embodiment depicted in the Figures, the device may be a toothbrush with a brush head (not shown) which may be, e.g. releasably, attached to the driven shaft 12. If a force is applied on the brush head the rocker frame 14 is pivoting about the axis IV defined by bar 16 and is displaced against the chassis of housing 4 and a PCB (not shown) mounted on the chassis of housing 4. This movement can be used to measure and control the applied pressure.

The eccentric pin 3 is rotating on a circle. The displacement to the side is the radius to the center of the motor axis I. For example with a radius of 1.5 mm, the side to side travel is ±1.5 mm. As the pin 3 is in a hole in the sliding block 5, the sliding block 5 moves the same distance. The cross slider 7 is oscillating in the brackets or links 8 and 9 and, thus, is moving on a radius of the distance of the links allowing the side to side motion. For example with a link length $L_1$ of 4.73 mm and an arm length $L_2$ of 4.5 mm, the lateral side motion d (in y direction) may be 1.5 mm Therefore, the oscillation angle phi being 19.5° may be calculated from the equation:

$$\sin(\text{phi}) = d/L_1 \quad (1)$$

The transvers motion t (in x direction) may be calculated from the equation:

$$t = L - L^* \cos(\text{phi}) \quad (2)$$

This results for the links 8, 9 with a length $L_1$ to $t_1$=0.257 mm and for the arm 13 with the length $L_2$ to $t_2$=0.244 mm.

Figure 6:
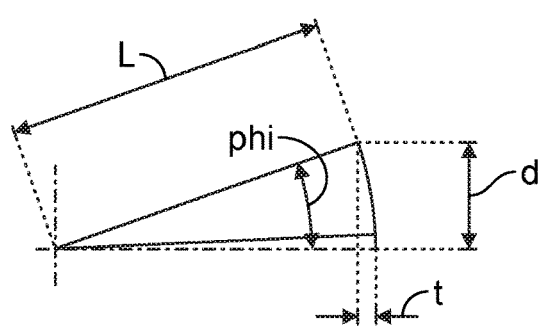
FIG. 6 schematically shows the correlation of values of the mechanism.

The effective value for the 3D motion is the difference in the values for t, i.e. Δt=0.257 mm-0.244 mm=0.013 mm FIG. 6 schematically shows the correlation for the values L, d, t and phi.

This motion is directed to the driven shaft 12 at the lower end and at a shorter distance to the pivoting axis IV (at pin 16) than the brush head (not shown). If, for example, the distance of the actuation to the pivoting axis is 29 mm and the distance from the pivoting axis to the brush head is 65 mm the resulting 3D motion will be 0.013 mm*65/29=0.27 mm. In reality the 3D motion may be a bit smaller than in the ideal mathematical model due to clearances in the joints and due to elasticity in the component parts. A 3D motion in the magnitude of for example 0.03 to 0.20 mm or up to 0.30 mm, in particular 0.04 mm to 0.1 mm, may be desirable for some toothbrushes. Other values may be desirable for different devices. The 3D motion occurs at twice the frequency of the driving frequency of the motor 1.

Figure 7:
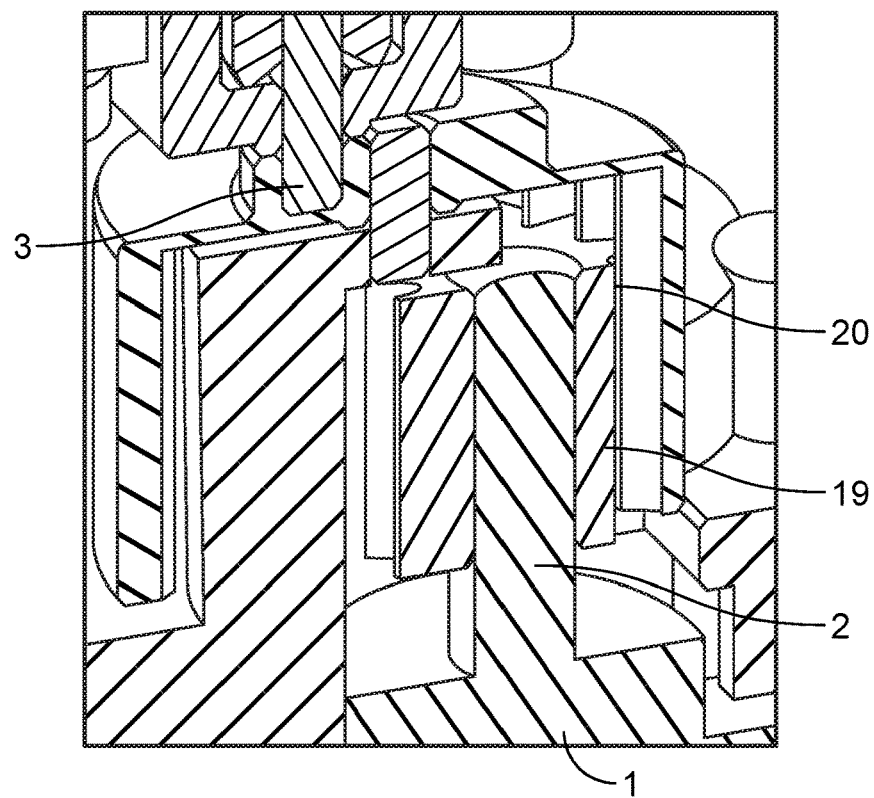
FIG. 7 shows a further embodiment of the drive pin coupled to the drive shaft by means of a gearing mechanism.

FIG. 7 shows an alternative arrangement of the drive pin 3 with respect to the drive shaft 2 of the motor 1. In this embodiment a further gear mechanism is interposed between the drive shaft 2 and the drive pin 3. In more detail, a pinion 19 is provided on the drive shaft 2 meshing with a ring gear 20 which in turn carries the drive pin 3. The gear ratio between the drive shaft 2 and the drive pin 3 may be adapted as required, e.g. depending from the torque and/or voltage of the motor 1.

Figure 8:
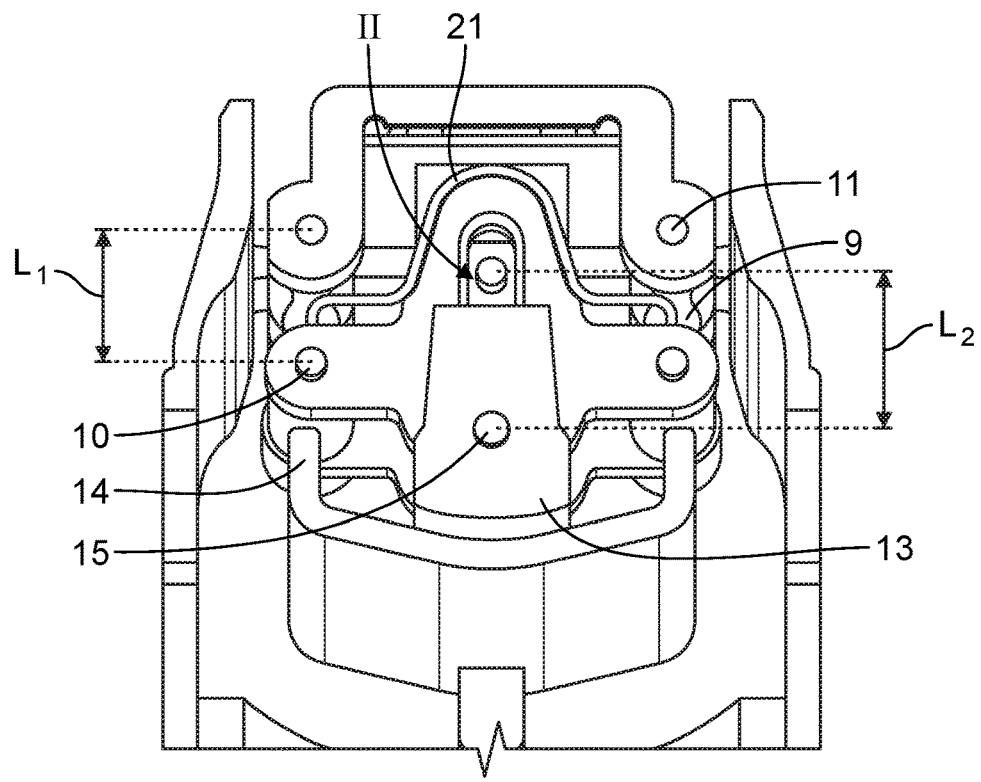
FIG. 8 shows a sectional view of a device according to a further embodiment.

If the lengths $L_1$ and $L_2$ are equal as depicted in the embodiment of FIG. 8, there is no active 3D motion of the shaft 12 because arm 13 and the links 8, 9 swivel in unison with identical values for t, i.e. without a Δt causing the 3D motion.

Caused by the change of the direction of slider movement additional noise may be generated in the bearing holes 10, 11 of the links 8, 9 due to the clearance in the holes. The contact surfaces between links and axles will change from one side to the other, according to the necessary bearing clearance. To avoid this knocking noise, it is useful to apply a defined load to the links, so that the links 8, 9 always are preloaded and are in close contact with the metal axles. FIG. 8 shows a spring 21 which is rotatably assembled to both links, so the spring 21 does not change load caused by the movement of the links. The distance between the two fixation points of the spring 21 in the links is independent of the angle of the links (rhomboid/parallelogram). The spring force which is applied to each bearing may be about 1N (the effective necessary load depends also on the frequency of the drive to achieve optimal results).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electrically driven device comprising
a housing (4),
an electric motor (1) mounted in the housing (4) and comprising a drive shaft (2) having a first rotary axis (I),
a driven shaft (12) having a second axis (II) and mounted in the housing (4) for performing a movement relative to the housing (4),
wherein the driven shaft (12) is indirectly coupled to the drive shaft (2) by means of a gear mechanism comprising a scotch yoke mechanism (5, 7) converting a rotary motion of the drive shaft (2) into an oscillating motion of the driven shaft (12),
wherein
a drive pin (3) is connected to the drive shaft (2) eccentrically with respect to the rotary axis (I), the scotch yoke mechanism comprises a cross slider (7) having a sliding support (6) which extends perpendicular to the first rotary axis (I) and which receives the drive pin (3) either directly or by means of a sliding block (5) having a bearing receiving the drive pin (3), wherein the cross slider (7) is guided in the housing (4) by means of at least two pivotable links (8, 9), and
the driven shaft (12) is coupled to the cross slider (7) by means of a pivotable arm (13), thereby converting a rotary motion of the drive shaft (2) into an oscillating motion of the driven shaft (12),
wherein each of the at least two pivotable links (8, 9) is pivotably hinged to a bearing point (10) of the housing (4) and pivotably hinged to a bearing point (11) of the cross slider (7) such that the cross slider (7) is guided to be moveable on a curved track with respect to the housing (4),
wherein for each of the pivotable links (8, 9) a distance (L1) between the bearing point (10) of the housing (4) and the bearing point (11) of the cross slider (7) is identical,
wherein the distance (L1) of the pivotable links (8, 9) between the bearing point (10) of the housing (4) and the bearing point (11) of the cross slider (7) differs from a distance (L2) of the pivotable arm (13) between the bearing point (15) of the cross slider (7) and the second axis (II) of the driven shaft (12), and
wherein the driven shaft (12) is pivotably mounted in the housing (4) by means of a rocker frame (14) which is pivotable with respect to the housing (4) about a pivoting axis (IV) which is perpendicular to the first rotary axis (I) and perpendicular to an extension (III) of the sliding support (6).

2. The electrically driven device according to claim 1, wherein the pivotable arm (13) is pivotably hinged to a bearing point (15) of the cross slider (7) and rotationally constrained to an anchorage point of the driven shaft (12).

3. The electrically driven device according to claim 2, wherein the distance ($L_1$) of the pivotable links (8, 9) between the bearing point (10) of the housing (4) and the bearing point (11) of the cross slider (7) is identical to the distance ($L_2$) of the pivotable arm (13) between the bearing point (15) of the cross slider (7) and the second axis (II) of the driven shaft (12).

4. The electrically driven device according to claim 1, wherein the distance ($L_1$) of the pivotable links (8, 9) between the bearing point (10) of the housing (4) and the bearing point (11) of the cross slider (7) is identical to the distance ($L_2$) of the pivotable arm (13) between the bearing point (15) of the cross slider (7) and the second axis (II) of the driven shaft (12).

5. The electrically driven device according to claim 1, wherein an elastically deformable element (17) is provided between the housing (4) and the rocker frame (14) biasing the rocker frame (14) into a rest position with respect to the housing (4).

6. The electrically driven device according to claim 5, wherein the switch or sensor is arranged in the housing (4) such that the switch or sensor detects movement of the rocker frame (14) with respect to the housing (4) exceeding a threshold movement.

7. The electrically driven device according to claim 5, wherein movement of the cross slider (7) generates an intermittent force ($F_X$) in a direction perpendicular to the axial movement of the cross slider (7) which intermittent force ($F_X$) is transmitted to the rocker frame (14) via the pivotable arm (13) and the driven shaft (12), with the intermittent force ($F_X$) biasing the rocker frame (14) away from the rest position.

8. The electrically driven device according to claim 7, wherein the intermittent force ($F_X$) generated by the motion of the cross slider (7) exceeds the biasing force ($F_Y$) of the elastically deformable element (17).

9. The electrically driven device according to claim 8, wherein if the rocker frame (14) is in its rest position with respect to the housing (4) with the elastically deformable element (17) being unstressed, a user force is exerted on the driven shaft (12) is directed opposite to the intermittent force ($F_X$) generated by the motion of the cross slider (7).

10. The electrically driven device according to claim 1, wherein a switch or sensor is provided and arranged in the housing (4) such that the switch or sensor detects movement of the rocker frame (14) with respect to the housing (4).

11. The electrically driven device according to claim 1, wherein a first transmission stage of the gear mechanism converts a continuous rotary motion of the drive shaft (2) into a sinusoidal reciprocating displacement of the cross slider (7).

12. The electrically driven device according to claim 1, wherein a bar (18) is provided constrained to the housing (4) and located at the end of the driven shaft (12) facing towards the motor (1).

* * * * *